United States Patent [19]
Abouleish

[11] Patent Number: 5,830,188
[45] Date of Patent: Nov. 3, 1998

[54] CURVED CANNULA FOR CONTINUOUS SPINAL ANESTHESIA

[75] Inventor: Ezzat I. Abouleish, Houston, Tex.

[73] Assignee: Board of Regents, The University of Texas System, Austin, Tex.

[21] Appl. No.: 763,454

[22] Filed: Dec. 11, 1996

[51] Int. Cl.⁶ .................................................. A61M 5/178
[52] U.S. Cl. ........................ 604/158; 604/161; 604/164; 604/264
[58] Field of Search .............................. 604/51, 53, 158, 604/161, 164, 165, 264, 280–282

[56] References Cited

U.S. PATENT DOCUMENTS

| | | |
|---|---|---|
| 4,543,090 | 9/1985 | McCoy . |
| 4,753,223 | 6/1988 | Bremer . |
| 4,776,844 | 10/1988 | Ueda . |
| 4,925,445 | 5/1990 | Sakamoto et al. . |
| 4,984,581 | 1/1991 | Stice . |
| 5,019,040 | 5/1991 | Itaoka et al. . |
| 5,025,799 | 6/1991 | Wilson . |
| 5,069,226 | 12/1991 | Yamauchi et al. . |
| 5,078,684 | 1/1992 | Yasuda . |
| 5,090,956 | 2/1992 | McCoy . |
| 5,106,376 | 4/1992 | Mononen et al. ........................ 604/164 |
| 5,114,402 | 5/1992 | McCoy . |
| 5,163,901 | 11/1992 | Eldor ........................................ 604/158 |
| 5,165,420 | 11/1992 | Strickland ................................. 604/19 |
| 5,183,470 | 2/1993 | Wettermann ............................. 604/281 |
| 5,232,422 | 8/1993 | Johnson et al. ............................ 604/51 |
| 5,238,004 | 8/1993 | Sahatjian et al. . |
| 5,304,141 | 4/1994 | Johnson et al. ........................... 604/158 |
| 5,330,466 | 7/1994 | Sahatjian et al. . |
| 5,334,168 | 8/1994 | Hemmer . |
| 5,345,937 | 9/1994 | Middleman et al. . |
| 5,389,073 | 2/1995 | Imran . |
| 5,395,327 | 3/1995 | Lundquist et al. . |
| 5,470,318 | 11/1995 | Griffith, III et al. .................... 604/161 |
| 5,478,330 | 12/1995 | Imran et al. . |
| 5,514,115 | 5/1996 | Frantzen et al. . |
| 5,591,132 | 1/1997 | Carrie ...................................... 604/158 |

Primary Examiner—Sam Rimell
Assistant Examiner—Robert V. Racunas
Attorney, Agent, or Firm—Akin, Gump, Strauss, Hauer & Feld, L.L.P.

[57] ABSTRACT

A substantially straight over-the-needle catheter comprising memory material and having a deviated tip may be packaged, shipped and stored for use in a deviated state so as to preserve the material memory. In preparing for use, the catheter is temporarily straightened using a catheter shield, after which a substantially straight inner needle is inserted (optionally through a guide needle). The catheter shield is removed prior to insertion of the catheter with its inner needle into a space within an anatomic structure. Subsequent removal of the inner needle allows the catheter to assume its deviated shape within the anatomic structure. The deviated catheter tends to be well retained in an anatomic structure, tends to reduce leakage of fluids from within the anatomic structural space, and allows predictable direction of fluid flow injected within the anatomic structural space.

11 Claims, 5 Drawing Sheets

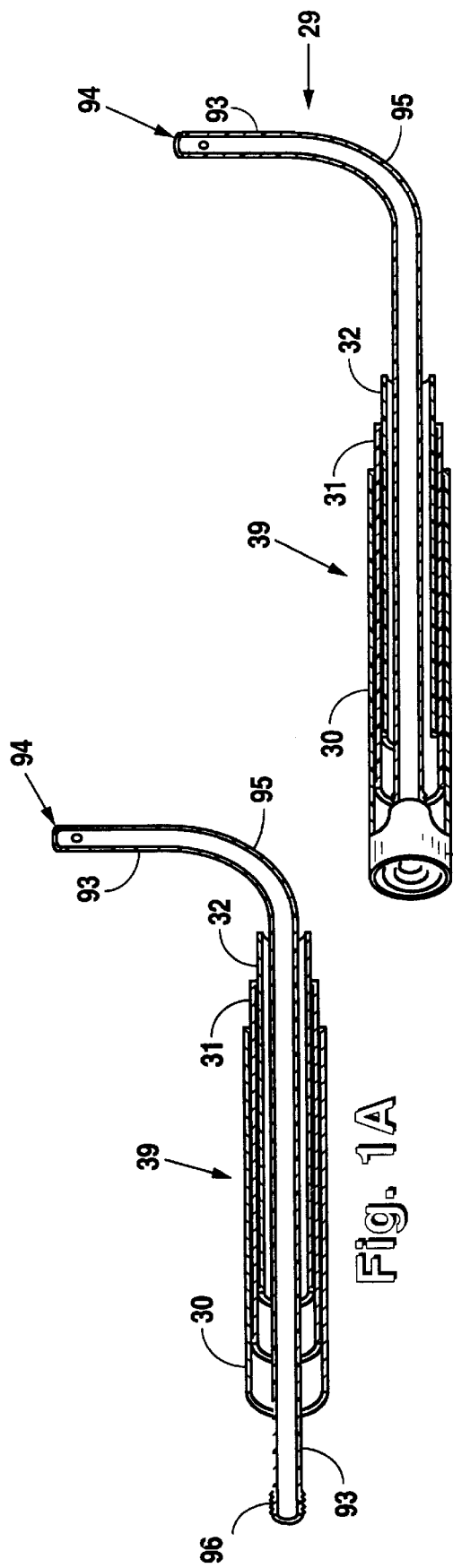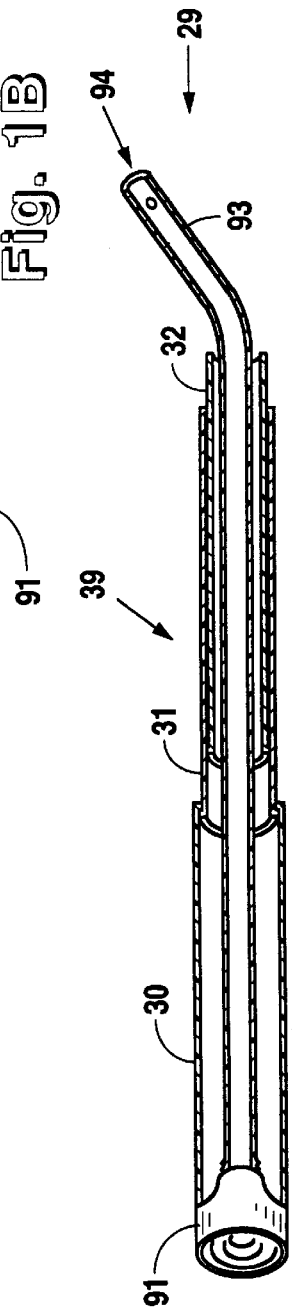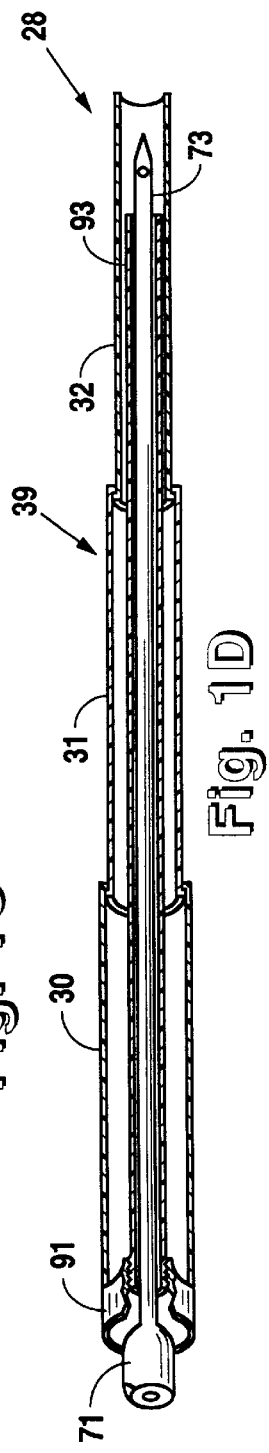

CURVED CANNULA FOR CONTINUOUS SPINAL ANESTHESIA

FIELD OF THE INVENTION

The present invention relates generally to the field of catheters and in particular to apparatus for placement and use of a catheter for administration of continuous spinal anesthesia.

BACKGROUND

Continuous spinal anesthesia is commonly achieved by inserting a catheter through the dura within the spinal canal so that it extends a relatively short distance into the subarachnoid space. Administration of one or more anesthetic drugs continuously or periodically through the catheter into the space can provide superior regional anesthesia over extended periods with relatively small total drug doses. But complications may occur for several reasons. For example, care is taken not to insert the catheter too far into the space to reduce the likelihood that it will become knotted and/or entangled in nerve tissue and thus be difficult to remove. With only a short length of catheter within the space, slight displacement of the back skin to which the catheter is usually taped can result in the catheter tip being withdrawn from the space. Since anesthetic drugs may not then be reliably injected into the subarachnoid space, the catheter must be withdrawn completely from the body and reinserted. A second dural puncture increases the likelihood of a postoperative postural headache.

Postural (or spinal) headaches are sometimes associated with continuous spinal anesthesia because insertion of a catheter to deliver the anesthetic drugs is usually through a relatively large-bore needle. The large-bore needle makes a relatively large hole in the dura on being directed into the subarachnoid space. This large hole predisposes the patient to a postural headache after the needle and catheter are removed and cerebrospinal fluid leaks out of the hole. Conservative measures to treat the headache (such as bed rest, hydration and/or a blood patch) may not be effective in stopping the leak, and in rare cases the continued leak may predispose the patient to development of a time-delayed intracranial subdural hematoma with significant neurological deficits.

Two other complications can arise from the relatively small diameter of the catheter which is necessitated by the requirement to thread it through a large-bore needle. Whereas aspiration of cerebrospinal fluid through the catheter is a good indication that the catheter tip is within the subarachnoid space, such aspiration is made more difficult and subject to error because of the small bore of through-the-needle spinal catheters. As a result, excessive catheter length may unintentionally be threaded into the subarachnoid space and may travel in unintended directions so as to impinge on the spinal cord blood supply and/or to mechanically damage nerves.

Difficulty in controlling the direction of tip travel of through-the-needle catheters is increased because the catheters are made very flexible in order to pass through the curved tip of a spinal needle. While a spinal needle thus gives initial (preferably cephalad) direction to the catheter, this direction is not always reliably maintained. If the catheter tip turns caudad and proceeds in that direction, the resulting anesthesia may be insufficiently high and/or it may require excessive amounts of anesthetic drugs. Drug overdose, in turn, may predispose the patient to a permanent block leading to a cauda equina lesion.

A significant amount of morbidity associated with the above complications might be avoided if the catheter bore might be increased without increasing the likelihood of cerebrospinal fluid leaks, if the position and direction of the catheter tip within the subarachnoid space could be better controlled, and if the catheter could be more reliably retained within the subarachnoid space.

SUMMARY OF THE INVENTION

The present invention comprises an assembly which itself comprises an over-the-needle catheter with an optional guide needle or introducer for penetrating relatively dense or tough material which overlies more easily penetrated material. The over-the-needle catheter comprises a deformable memory material (comprising, for example, such plastics as Teflon) in the shape of a substantially straight tube which is deviated proximate the distal tip, preferably through an arcuate bend which will turn a fluid stream moving through the tube (without significantly pinching off the stream) through an angle of about 90 degrees. The arcuate bend is curved to ensure that the bend is substantially complete (that is, the tube turns through about 90 degrees) within a distance substantially equal to the diameter of a vessel or analogous relatively unobstructed dimension of the structure into which the catheter may be inserted.

After insertion into a structure as above and withdrawal of the substantially straight needle within the catheter, the predetermined arcuate bend will form in the memory material. This bend, in conjunction with the relatively close fit established between the catheter and the overlying material through which it passes, will tend to retain the catheter within the structure into which it is inserted to a greater extent than a substantially straight catheter would be retained. Additionally, the bend proximate the distal catheter tip can serve to direct fluid injected through the catheter in a predetermined preferred direction. And the relatively close fit with overlying material can help reduce leakage of fluid from within the structure, both while the catheter remains inserted as well as after it is withdrawn.

Because it is desirable that the deformable memory material of a catheter tube of the present invention retain the above preferred distal deviation over the time between manufacture and use, the catheter is preferably packed, shipped and stored for use in a deviated (that is, bent) condition. During insertion into a structure, however, the catheter is preferably straight. Since a substantially straight inner needle which will slidingly fit within the catheter would tend to puncture the catheter wall if inserted while the catheter tube is deviated, the tube must be substantially straightened before such inner needle insertion.

The straightening function may be accomplished by manually placing the catheter within a catheter shield. The shield may take the form of a relatively stiff and substantially straight longitudinally closed outer tube into which the catheter is inserted (or which may alternatively be drawn over the catheter) temporarily while the inner needle is inserted. Note that this longitudinally closed outer tube may be one-piece or telescopic in form (the latter form including a plurality of longitudinally slidingly coupled pieces which retain a relatively fixed relationship to a longitudinal axis whether the pieces are telescoped together or extended along the longitudinal axis. Alternatively, the catheter may be pressed substantially laterally into a closely fitting relatively stiff and substantially straight tube having a substantially longitudinal slit (that is, a longitudinally open tube). Still another approach to temporary straightening of a deviated catheter tube prior to insertion of an inner needle would be substantially lateral placement (and temporary manual retention) of the tube within a substantially straight groove within a suitable substrate, such as a substantially rigid plastic block.

Thus, a catheter assembly of the present invention may comprise a catheter subassembly which itself comprises a catheter tube and hub, the tube having a proximal end and a distal tip and comprising deformable memory material. The distal tip is deformably deviated (preferably by about 90 degrees), and the catheter hub (comprising a rotational directional indicator referable to the direction of the above tip deviation) is reversibly attached to the catheter tube proximal end. An inner needle (preferably a spinal needle) fitting slidingly within the catheter hub and catheter tube, together with a catheter shield for straightening the catheter tube prior to insertion of the spinal needle within the catheter tube facilitate preparing the catheter assembly for insertion. A guide needle (preferably an epidural needle) fitting slidingly over the catheter tube completes the catheter assembly, but in other preferred embodiments of the invention, the above catheter subassembly may be augmented with a catheter shield (as described herein) for straightening the catheter tube, thus forming a catheter-shield subassembly. Insertion of a substantially straight inner needle within the catheter tube of a catheter-shield subassembly forms a catheter-shield-needle subassembly.

The invention also includes a method of inserting into an anatomic structure a catheter having a catheter tube with a deformably deviated distal tip. The method comprises straightening the catheter tube distal tip with a catheter shield and inserting a slidably fitted inner needle having a point within the catheter, the needle point projecting beyond the catheter tube distal tip. After the catheter shield is removed to form an insertable catheter, the insertable catheter is inserted into an anatomic structure (optionally through a guide needle) and the (inner) needle is removed from the insertable catheter, leaving the catheter inserted into the anatomic structure. In cases where the optional guide needle is used, one may remove it by first removing the (reversibly attachable) catheter hub after the inner needle is removed and then sliding the guide needle off the proximal (or hub) end of the catheter tube. This action assumes that the reversible nature of the hub-catheter attachment is achieved via corresponding threaded portions of the tube and hub, by an interference fit, by a clamp, or by analogous substantially liquid-tight mechanical connection, any of which would leave the catheter tube in condition to allow the sliding removal of the guide needle over the area of attachment.

BRIEF DESCRIPTION OF THE DRAWINGS

FIG. 1A schematically illustrates a telescopic catheter shield over a substantially straight catheter tube with a deviated distal tip, the shield pieces being telescoped together (partial cross-section).

FIG. 1B schematically illustrates the telescopic catheter shield and catheter tube of FIG. 1A with the addition of a catheter hub reversibly attached to the catheter tube (partial cross-section).

FIG. 1C schematically illustrates the telescopic catheter shield, catheter tube, and catheter hub of FIG. 1B with the middle shield piece extended over the catheter tube to partially straighten the tube (partial cross-section).

FIG. 1D schematically illustrates the telescopic catheter shield, catheter tube, and catheter hub of FIG. 1C with the inner shield piece extended over the catheter tube to substantially straighten the tube (partial cross-section).

DETAILED DESCRIPTION

Figure 2:
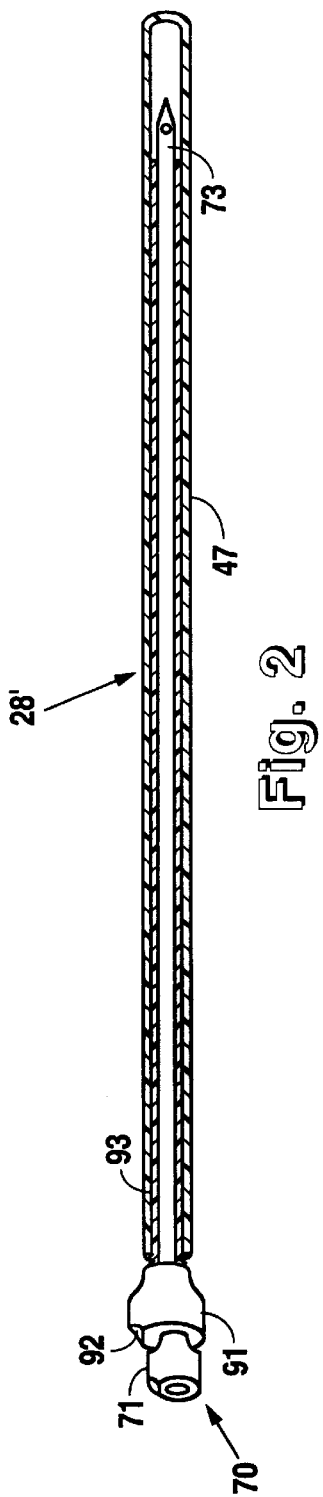
FIG. 2 schematically illustrates a catheter-shield subassembly over a substantially straight inner needle wherein the shield comprises a one-piece longitudinally closed tube (partial cross-section).
Figure 3A:
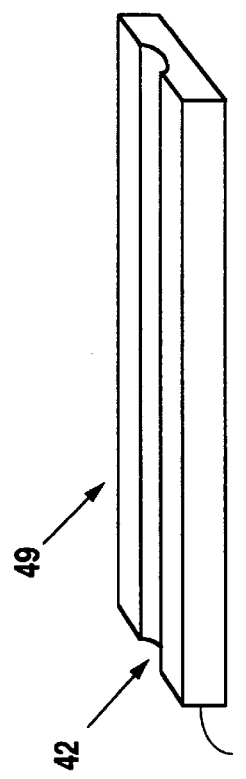
FIG. 3A schematically illustrates a groove type shield in a substantially rigid block.
Figure 3B:
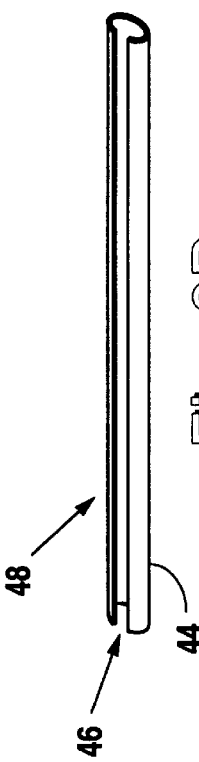
FIG. 3B schematically illustrates a longitudinally open tube type shield.
Figure 3C:
FIG. 3C schematically illustrates a longitudinally closed tube type shield.

As shown in FIGS. 1–6, a catheter assembly of the present invention may comprise a catheter subassembly 98 which itself comprises a catheter tube 93 and hub 91, the tube 93 having a proximal end 96 and a distal tip 94 and comprising deformable memory material. The distal tip 94 is deformably deviated (preferably by about 90 degrees through an arcuate bend 95), and the catheter hub 91 (comprising a rotational directional indicator 92 referable to the direction of the above tip deviation) is reversibly attached to the catheter tube proximal end 96. Although threads are schematically illustrated on proximal catheter tube end 96 in FIG. 1A, alternative attachments may be used to join the catheter hub 91 and catheter tube 93 in a liquid-tight manner, as described above. An inner needle 70 comprising an inner needle hub 71 and a substantially straight inner needle shaft 73 (preferably in the form of a spinal needle) fits slidingly within the catheter hub 91 and catheter tube 93. A catheter shield 39,47,48,49 straightens the distally deviated catheter tube 93 prior to insertion of the inner needle shaft 73 within the catheter tube 93, thus facilitating preparation of the catheter assembly for insertion. A guide needle 60, comprising a guide needle hub 61 and a substantially straight guide needle shaft 63, (preferably an epidural needle) fits slidingly over the catheter tube 93 to complete the catheter assembly.

Note that in other preferred embodiments of the invention, the above catheter subassembly 98 may be augmented with a catheter shield (as described herein) for straightening the catheter tube, thus forming a catheter-shield subassembly 29, schematically illustrated with a telescoping shield 39 in FIGS. 1(B–C). Insertion of a substantially straight inner needle 70 within the catheter tube 93 of a catheter-shield subassembly forms a catheter-shield-needle subassembly 28,28', schematically illustrated with a telescoping longitudinally closed tubular shield 39 in FIG. 1D and with a one-piece longitudinally closed tubular shield 47 in FIG. 2.

The invention also includes a method of inserting into an anatomic structure (such as the subarachnoid space 56) a catheter subassembly 98 having a catheter tube 93 with a deformably deviated distal tip 94. The method comprises straightening the catheter tube distal tip 94 with a catheter shield 39,47,48,49 and inserting a slidably fitted inner needle 70 having a point 75 within the catheter subassembly 98, the needle point 75 projecting beyond the catheter tube distal tip 94. After the catheter shield 39,47,48,49 is removed to form an insertable catheter 15, the insertable catheter 15 is inserted into an anatomic structure. An example anatomic structure schematically illustrated comprises the skin and subcutaneous tissues 50, the ligamentum flavum 52, and the dura 54 lying within the spinal canal and surrounding the subarachnoid space 56.

Figure 4:
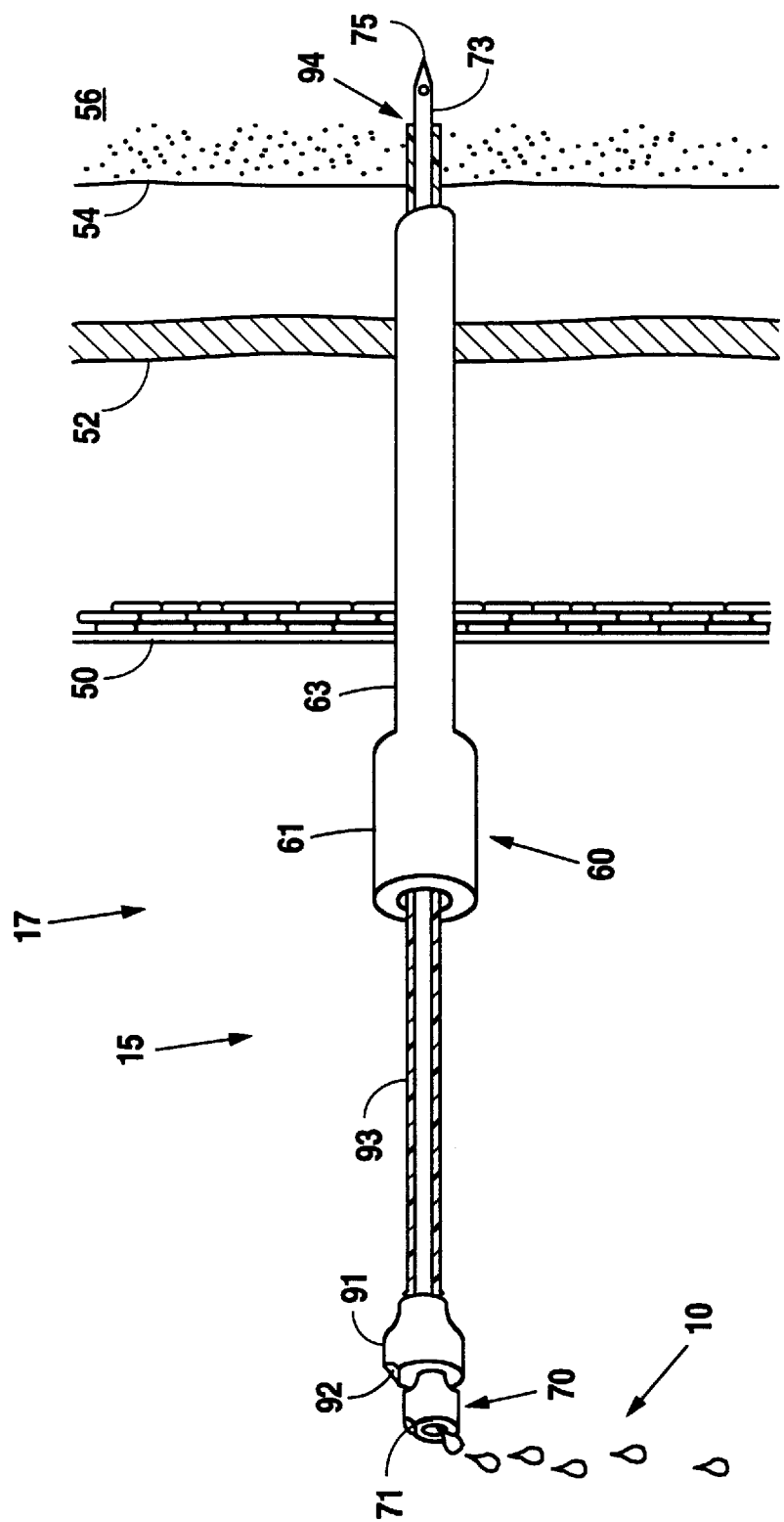
FIG. 4 schematically illustrates a catheter subassembly over a substantially straight inner needle, the subassembly passing through an epidural guide needle and into the subarachnoid space (phantom view).
Figure 5:
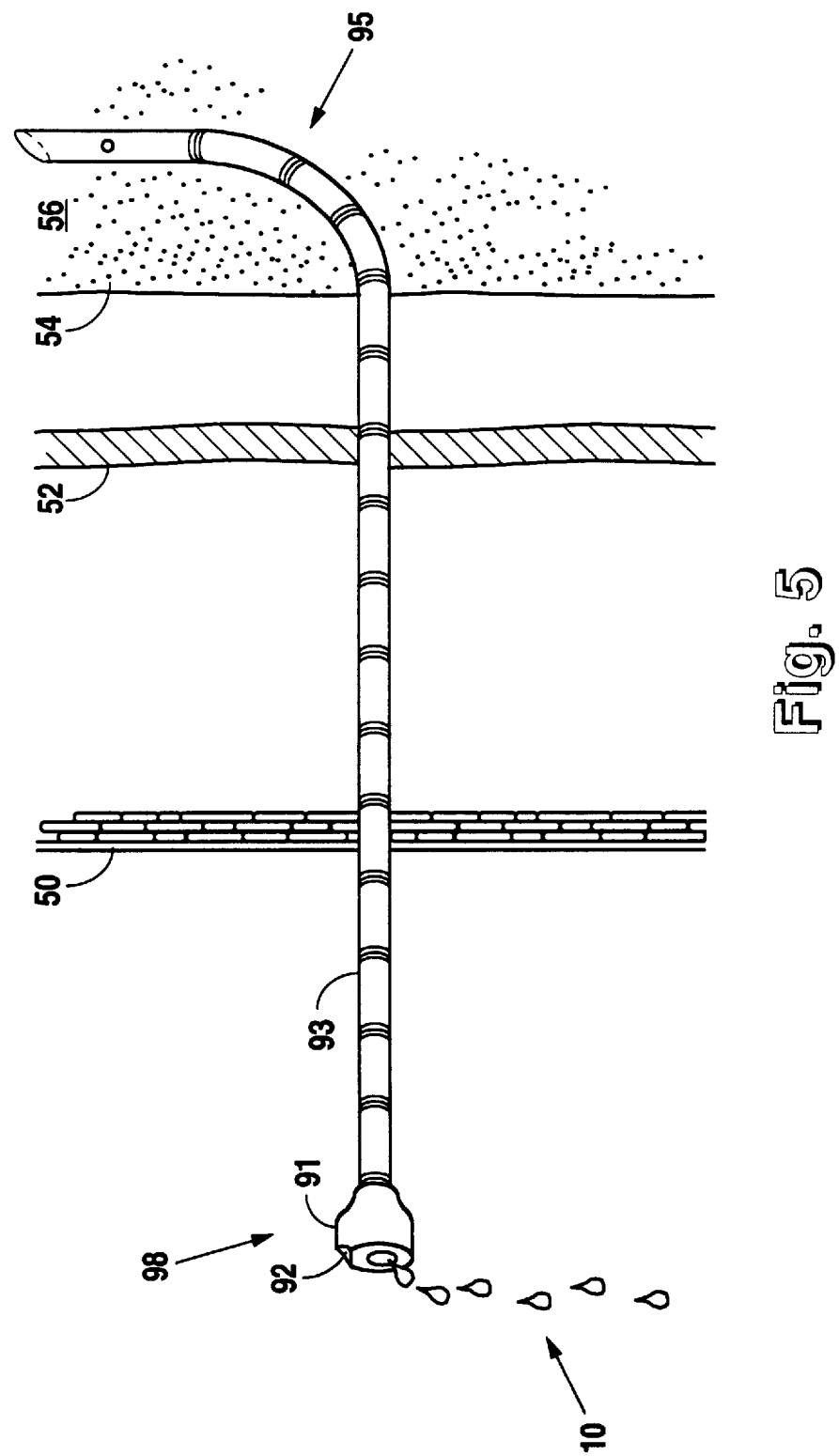
FIG. 5 schematically illustrates the catheter subassembly of FIG. 4 with the catheter tube advanced and the inner needle withdrawn to allow the distal catheter deviation to become apparent.
Figure 6:
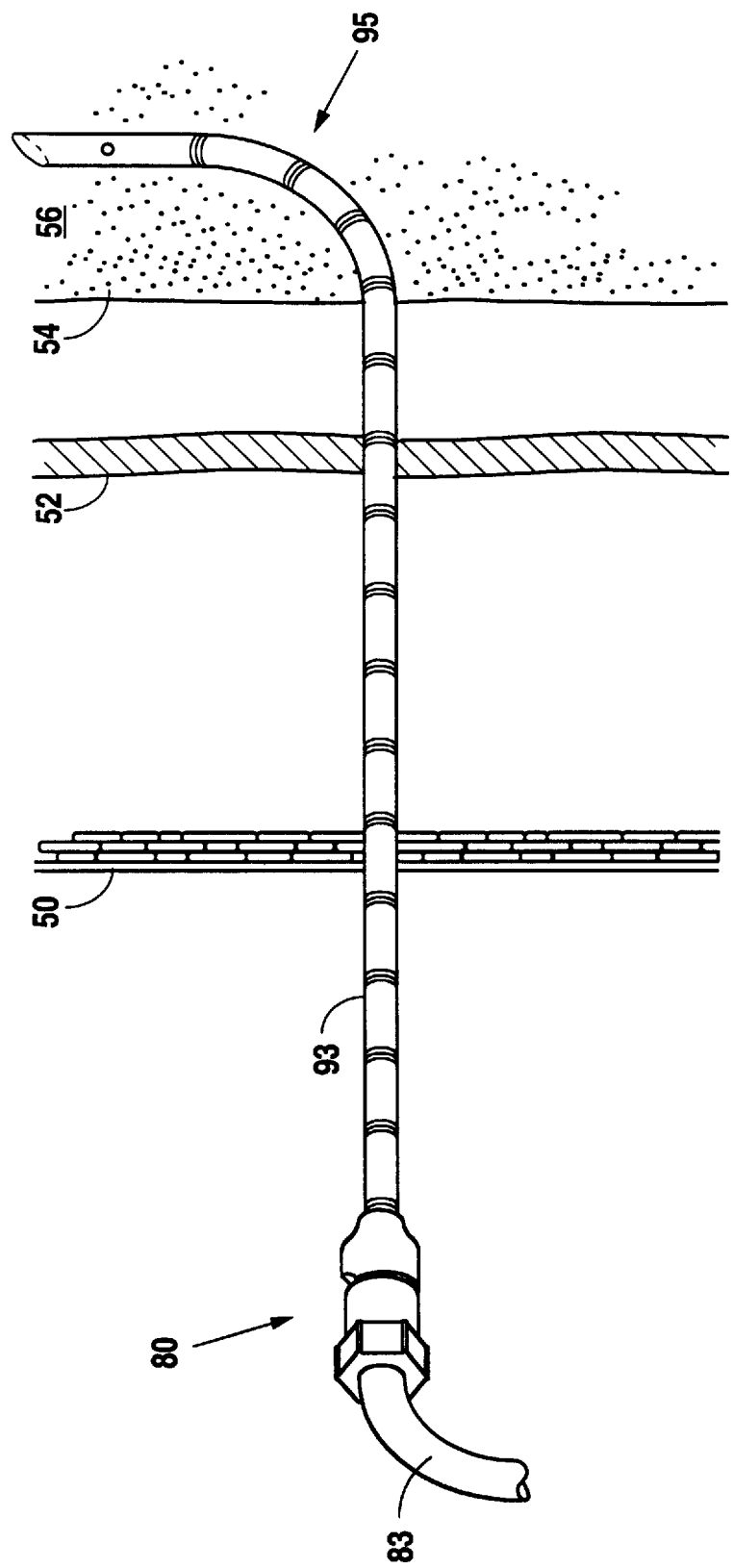
FIG. 6 schematically illustrates the catheter subassembly of FIG. 5 after removal of the catheter hub and connection of the catheter tube to extension tubing which may be connected in turn to an external fluid source.

Insertion of the insertable catheter 15 into the subarachnoid space 56 is optionally through a guide needle 60, forming an insertable catheter subassembly 17. Guide needle 60 is used to pierce the material (skin 50 and ligamentum flavum 52) relatively resistant to puncture which overlies the material more easily punctured (dura 54). The inner needle 70 is removed from the insertable catheter 15, leaving the catheter subassembly 98 inserted into the anatomic structure (the subarachnoid space 56 in FIGS. 4–6). Proper placement of inner needle 70 with catheter subassembly 98 within the subarachnoid space 56 is schematically indicated in FIG. 4 by dripping of cerebrospinal fluid 10 from inner needle hub 71. After removal of inner needle 70 from the insertable catheter 15, proper placement of catheter tip 94 within the subarachnoid space 56 is schematically indicated in FIG. 5 by dripping of cerebrospinal fluid 10 from catheter hub 91. In cases where the optional guide needle 60 is used, one may remove it by first removing the (reversibly attachable) catheter hub 91 after the inner needle 70 is removed and then sliding the guide needle 60 off the proximal (or hub) catheter tube end 96. Catheter hub 91 may then be replaced in catheter subassembly 98 with a hub or connector to facilitate injection of liquids through catheter tube 93. As an example, a connector 80 for intravenous tubing 83 is schematically illustrated in FIG. 6 as reversibly attached to tube end 96 (hidden) to facilitate injection of anesthetic drugs into the subarachnoid space 56.

During insertion into an anatomic structure, the catheter subassembly 98 is preferably straight. Since a substantially straight inner needle 70 which will slidingly fit within the catheter subassembly 98 would tend to puncture the catheter (tube) wall 93 if inserted while the catheter tube 93 is deviated, the tube 93 must be substantially straightened before such inner needle 70 insertion.

The straightening function may be accomplished by manually placing the catheter subassembly 98 within a catheter shield 39,47,48,49. The shield may take the form of a relatively stiff and substantially straight longitudinally closed outer tube 39,47 into which the catheter subassembly 98 is inserted (or which may alternatively be drawn over the catheter) temporarily while the inner needle 70 is inserted. Note that this longitudinally closed outer tube 39,47 may be one-piece 47 or telescopic 39 in form. The latter form includes a plurality of longitudinally slidingly coupled pieces (pieces 30,31,32 are schematically illustrated as examples of one preferred embodiment in FIGS. 1(A–D)) which retain a relatively fixed relationship to a longitudinal axis whether the pieces are telescoped together (see FIG. 1A) or extended along the longitudinal axis (see FIG. 1D). Alternatively, the catheter subassembly 98 may be pressed substantially laterally into a closely fitting relatively stiff and substantially straight tube 44 having a substantially longitudinal slit 46 (that is, a longitudinally open tube 48). Still another approach to temporary straightening of a deviated catheter tube 93 prior to insertion of an inner needle 70 would be substantially lateral placement (and temporary manual retention) of the tube 93 within a substantially straight groove 42 within a suitable substrate such as a substantially rigid plastic block 40 (that is, an open groove catheter shield 49).

I claim:

1. A catheter assembly, comprising a catheter subassembly comprising a catheter tube having a proximal end and a distal tip and comprising deformable memory material, said distal tip being deformably deviated to form a bend; and a catheter hub comprising a rotational directional indicator aligned with said tip and said bend, said hub being reversibly attachable to said catheter tube proximal end;

an inner needle fitting slidingly within said catheter hub and catheter tube;

a catheter shield for straightening said catheter tube prior to insertion of said inner needle within said catheter tube; and a guide needle fitting slidingly over said catheter tube.

2. The catheter assembly of claim 1 wherein said inner needle is a spinal needle.

3. The catheter assembly of claim 1 wherein said guide needle is an epidural needle.

4. The catheter assembly of claim 1 wherein said distal tip is deviated about 90 degrees.

5. The catheter assembly of claim 1 wherein said deformable memory material comprises plastic.

6. The catheter assembly of claim 1 wherein said catheter shield is telescopic.

7. The catheter assembly of claim 1 wherein said catheter shield comprises a substantially straight longitudinally closed tube.

8. The catheter assembly of claim 1 wherein said catheter shield comprises a substantially straight longitudinally open tube.

9. The catheter assembly of claim 1 wherein said catheter shield comprises a substantially straight grooved substrate.

10. A method of inserting into an anatomic structure a catheter having a catheter tube with a deformably deviated distal tip, the method comprising straightening the catheter tube distal tip with a catheter shield;

inserting a slidably fitted inner needle having a point within the catheter, said needle point projecting beyond the catheter tube distal tip;

removing said catheter shield to form an insertable catheter;

inserting said insertable catheter into a slidably fitted guide needle to form an insertable catheter assembly, said guide needle not projecting beyond the catheter tube distal tip;

inserting said insertable catheter assembly into an anatomic structure;

rotationally adjusting said deviated distal tip; and removing said inner needle from said insertable catheter, leaving said catheter inserted into the anatomic structure.

11. A method of inserting into an anatomic structure a catheter having a reversibly attachable catheter hub and a catheter tube with a deformably deviated distal tip, the method comprising straightening the catheter tube distal tip with a catheter shield;

inserting a slidably fitted inner needle having a point within the catheter, said needle point projecting beyond the catheter tube distal tip;

removing said catheter shield to form an insertable catheter;

inserting said insertable catheter into a slidably fitted guide needle to form an insertable catheter subassembly, said guide needle not projecting beyond the catheter tube distal tip;

inserting said insertable catheter assembly into an anatomic structure;

rotationally adjusting said deviated distal tip;

removing said inner needle from said insertable catheter, leaving said catheter inserted into the anatomic structure;

removing said reversibly attachable catheter hub; and removing said guide needle by sliding over said catheter hub attachment.

* * * * *